United States Patent [19]
Shim et al.

[11] 4,205,238
[45] May 27, 1980

[54] DIGITAL ELECTRONIC APPARATUS AND CASETTE SIZED FOR INTRAVENOUS FLUID-FLOW LIMITING EQUIPMENT

[75] Inventors: Norman Shim, Glenview; Vincent L. Knigge, Mundelein, both of Ill.

[73] Assignee: Baxter Travenol Laboratories, Inc., Deerfield, Ill.

[21] Appl. No.: 878,846

[22] Filed: Feb. 17, 1978

[51] Int. Cl.$^2$ .................. G06M 3/02; A61M 5/14
[52] U.S. Cl. .................. 235/92 CT; 235/92 FL; 235/92 T; 128/214 E; 222/207
[58] Field of Search ....... 235/92 CT, 92 FQ, 92 DM, 235/92 PE, 92 FL, 92 MS, 92 T; 128/214 E, DIG. 13; 222/70

[56] References Cited
U.S. PATENT DOCUMENTS

| | | | |
|---|---|---|---|
| 3,750,603 | 8/1973 | Martin | 235/92 CT |
| 3,876,869 | 4/1975 | Houpt | 235/92 T |
| 3,890,968 | 6/1975 | Pierce et al. | 128/214 E |
| 3,985,133 | 10/1976 | Jenkins et al. | 128/214 E |
| 4,016,407 | 4/1977 | Mesecar et al. | 235/92 T |
| 4,037,598 | 7/1977 | Georgi | 128/214 E |
| 4,038,981 | 8/1977 | Le Feure et al. | 128/214 E |
| 4,121,584 | 10/1978 | Turner et al. | 222/207 |

*Primary Examiner*—Joseph M. Thesz
*Attorney, Agent, or Firm*—Paul C. Flattery; John P. Kirby, Jr.; Garrettson Ellis

[57] ABSTRACT

A crystal-controlled low-frequency power-conserving circuit for use in a controller operating with a casette to limit the rate of flow of an intravenous solution to a patient. The circuit uses a crystal oscillator operating below the stray frequencies often present in a hospital environment. The CMOS components in the circuit respond to the low frequencies of the oscillator, display no sensitivity to the higher stray frequencies, and consume a minimum of energy. Binary rate dividers reduce the frequency obtained from the oscillator by a positive integral power of two. Cascaded variable binary rate multipliers selectively permit the absorbtion of a least half of the pulses received from the rate divider. The inverted pulses of the binary rate multipliers pass to the S input of a D-type flip-flop. The pulses from the binary divider pass to the C input of the same flip-flop. On a pulse from the rate multiplier, the Q output of the flip-flop provides a positive pulse to a monostable multivibrator which then briefly turns on current to the coil of an electromagnet to allow fluid to enter the cassette. The monostable multivibrator allows current to flow for the short period of time required to change the position of an armature pivotably coupled to the electromagnet. After the flip-flop subsequently receives two pulses from the rate divider, its Q output goes negative and the $\bar{Q}$ output becomes positive. This allows another monostable multivibrator to provide a brief pulse of current, in the opposite direction, to the electromagnet to return the armature to the first position. The fluid in the casette may thus flow to the patient.

40 Claims, 4 Drawing Figures

DIGITAL ELECTRONIC APPARATUS AND CASETTE SIZED FOR INTRAVENOUS FLUID-FLOW LIMITING EQUIPMENT

CROSS-REFERENCES TO RELATED APPLICATIONS

The controller discussed in the subject application may make use of the Z-shaped bracket in the design patent application of Nicholas Zissimopoulous entitled "Casette Holder and Transporter in a Fluid Flow Limiting Device", U.S. Application Ser. No. 878,965, filed Feb. 17, 1978, now abandoned. It may also utilize the mechanical components disclosed in the pending patent application "Improved Fluid-Flow Limiting Apparatus for Use With Intravenous Solution Administering Equipment" of Nicholas Zissimopoulous, Application Ser. No. 878,970, filed Feb. 17, 1978; the electromagnetic device of the patent application "Low-Current E-Frame Electronic Magnet With a Permanent Magnet Armature for an I.V. Valving Controller" of Orest Hrynewycz, Patent Application Ser. No. 878,650 filed Feb. 17, 1978; and either of the electromagnet shapes displayed in the design patent applications "E-Frame Electromagnet Having a Permanent Magnet Rocker-Arm Armature" of Orest Hrynewycz, U.S. Application Ser. No. 878,649, filed Feb. 17, 1978 and now abandoned; and "E-Frame Electromagnet Having Permanent Magnets Attached to a Rocker-Arm Armature" of Nicholas Zissimopoulous, Application Ser. No. 878,832, filed Feb. 17, 1978 and now abandoned. In addition to aspects of the above applications, the casette in the subject application may utilize a structure including the elastomeric membrane discussed in the pending patent application "Casette for Use With an I.V. Infusion Controller" of Scott T. Garrett, Lee K. Kulle and William L. Rudzena, Application Ser. No. 878,966, filed Feb. 17, 1978; the valving configurations of the pending patent application "Non-Critically Aligned Valving Devices for Flow Rate Limiting Casette Used in Intravenous Solution Administering Equipment" of Scott T. Garrett, Thurman S. Jess, Vincent L. Knigge, Lee K. Kulle, William L. Rudzena and Nicholas Zissimopoulous, U.S. Application Ser. No. 878,847, filed Feb. 17, 1978; and the shape shown in the design patent application "Valvable Casette" of Lee K. Kulle and William L. Rudzena, Ser. No. 878,962, filed Feb. 17, 1978, and now abandoned. All of these referenced applications have the same filing date as the subject application.

BACKGROUND

R. Scott Turner et al., in their U.S. patent application Ser. No. 732,946, now U.S. Pat. No. 4,121,584 entitled "Method and Apparatus for Controlling the Dispensing of Fluid" provide a significant development in controlling the rate at which an intravenous solution flows to a patient. They place a casette having a metering chamber with an inlet and an outlet in the fluid path taken by the solution as it travels to the recipient. A controller engages the casette and operates its valves. By opening the inlet and closing the outlet, the controller allows a metering chamber of known volume in the casette to fill with intravenous solution. It then closes the inlet and opens the outlet to allow that fluid to flow to the patient. It completes a cycle of operation by closing the outlet, opening the inlet, and allowing further fluid to flow into the metering chamber.

The controller includes a selection device which allows the attendant to choose the maximum rate at which the patient should receive the intravenous solution. In response to the selection thus made, the controller repeats the cycles of operation at an appropriate frequency. As a result, the separate aliquots of fluid equal in volume to the metering chamber will allow the patient to receive the desired amount of fluid during a period of time.

Turner et al.'s apparatus does not force the fluid to pass to the patient. Gravity provides the motive force causing the solution to flow. Where the fluid has an insufficient height above the point of administration, it will not pass to the patient, notwithstanding the inclusion of Turner et al.'s apparatus.

However, the equipment does serve to place an upper limit on the rate of flow of the fluid. It only allows a predetermined number of measured volumes to enter the patient's blood stream. That represents the critical limitation in the administration of intravenous solutions to an individual. If the patient receives the liquid at an excessive rate, he can suffer deleterious consequences. Even ordinary isotonic intravenous solution with only nutrients added can effectuate an unacceptable thinning of the patient's blood. Tissues depending upon the biochemicals in the blood stream can suffer when the excessive I.V. solution prohibits them from receiving these biochemicals in the required concentrations.

Excessive flow rates of intravenous solutions including medication can have drastically destructive effects upon the recipient. An inordinate concentration of the medication within the blood produces toxic effects upon the individual.

A dramatically superior casette appears in the patent application of Scott T. Garrett et al., referenced above under the title "Casette for Use with an I.V. Infusion Controller". These inventors provide a casette which sandwiches an elastomeric membrane between two sections of a rigid material, such as a plastic. The membrane forms part of the metering chamber as well as its inlet and outlet. The valving members, or rods, on the controller merely have to deform the membrane to close the appropriate opening. As a result, the controller need expend minimal energy to effectively operate the casette.

During each cycle of the operation, the controller must only move each valve member once in each of two directions. Moreover, the two valve members can couple together so that the motion of one in either direction directly accompanies the motion of the other in the opposite direction. Under these circumstances, the controller need only produce two almost insignificant motions during each cycle of operation.

With its light workload, the controller requires minimal energy to operate. Consequently, it may make use of a battery and can dispense with a direct connection to a constant source of electric power. This disencumbers the controller and allows it to travel wherever the needs of the patient may take it. Thus, it may find use at the scenes of accidents as well as accompany patients as they move about a hospital.

The longevity of a battery in the controller determines the desirability and practicality of disconnecting the controller from a constant supply of electric potential. Increasing the battery life portends the greater utilization of these devices with the concommittently increased safety for the patient.

In addition to utilizing minimal amounts of energy, the circuit should remain insensitive to broadcasted pulses of electrical energy having any appreciable strength in its environment. Additionally, the circuit must use reliable components but yet ensure that the appropriate valves in the casette remain open for sufficient periods of time.

SUMMARY

The casette discussed above typically has a metering means, or chamber, for holding a predetermined volume of fluid. A closable inlet and a closable outlet, both in fluid communication with the metering chamber, permits the flow of the fluid into and out of the metering means, respectively To operate this casette, the controller has a first valving member movable between a first and a second position. When in the second position, it closes the casette's inlet. A second member similarly moves between a third and a fourth position. In the latter, it closes the outlet. A moving device then couples to the above two valving members. It moves the first member between its first and second positions and the second member between its third and fourth positions.

Lastly, the controller includes a regulator coupled to the moving means. It assures that the operation of the moving device provides the desired rate of flow of the intravenous solution.

To avoid interference from electromagnetic waves generated by other equipment, the regulator should include a crystal controlled oscillator which produces digital pulses. The pulse rate should have a predetermined frequency of less than one megahertz.

The regulating circuit then includes a digital gate coupled to the oscillator. This gate reduces the pulse rate produced by the crystal oscillator to a frequency which can find direct use in inducing motion of the valving members. Upon the receipt of pulses at the first frequency produced by the oscillator, the gate provides output pulses at a second frequency of less than half the crystal oscillator's frequency. Typically, the gate's frequency will lie orders of magnitude lower than the oscillator's.

Lastly, a responding device forms part of the regulator. It couples to the digital gate and to the moving means. When it receives an output pulse from the gate, it causes the moving means to move either the first valving member between its two positions or the second valving member between its positions.

Typically, the two valving members couple to a single moving portion of the moving means. Whenever one moves, both do so at approximately, though not exactly, the same time. Furthermore, when one of the valve members opens its opening, the other member typically closes the other opening. Consequently, if the moving means moves the first member to close the inlet it also moves the second valving member to open the outlet. Moving in the reverse direction, it produces the opposite effect for both the valving members.

The responding device may include a D-type flip-flop receiving two inputs from the digital gate. It receives one type of output pulse from the digital gate when the inlet should open and the outlet should close. It receives a second type of output pulse from the digital gate when the inlet should close to allow the outlet to open.

Typically the digital gate includes two sections. The first simply divides the frequency of the crystal controlled oscillator by a constant factor. It produces a substantially square-wave pulse train in which the duration of the upper voltage level substantially equals the duration of the lower level. The pulse frequency in this square-wave pulse train typically reaches a sufficiently low level that it finds direct use in guiding the controller's operation.

Most economically, this divider section of the digital gate may divide the pulse-train frequence by a positive integral power of two. This binary division exploits the binary character of most logic components and achieves its result with a minimum of electronic devices and power consumption.

The second section of the digital gate permits the selection of the actual amount of fluid, within preset limits, that the patient may receive. Operating upon the pulses received from the divider, it provides output pulses of its own. The number of such output pulses will cause the moving means to move the valve members a sufficient number of times so that the desired amount of fluid per hour reaches the patient.

One type of variable rate divider uses rotary wheel switches coupled to cascaded binary rate multipliers. The switches have the digits from 0 to 9 appearing on them corresponding to differing configurations of electrical contacts within the switch. The cascaded rate multipliers then provide a number of output pulses depending upon the digits dialed on the switches. For example, using three switches with the digits x, y, and z selected on them, the rate multiplier will provide xyz output pulses for each 1000 input pulses. Thus, specifically dialing 167 on the switches will cause the rate multipliers to produce 167 output pulses for each 1000 of the input pulses.

For the administration of intravenous fluid, the amount of fluid received by the patient should remain within the range of about 18 to 199 ml. per hour. Using the rotary switches for these numbers, the binary rate multipliers can produce only 199 output pulses for each 1000 input pulses received.

Alternatively, the controller can employ a circuit that utilizes all of the pulses received by the constant divider to control the actions of the moving means. In other words, the thumb wheel switches with the cascaded rate multipliers discards 801 for every 1000 pulses where 199 represents the upper limit that can be selected. A circuit using electronic selection devices could utilize all of the pulses that it receives and not necessarily need to discard any.

The amount of fluid received by the patient depends upon the volume that the casette delivers on each of its cycles of operation. Consequently, it must have a specific deliverable volume which, when passed the number of times determined by the available pulses, closely approximates the desired volume per hour.

However, controllers may use either of the two variable dividers enumerated above. Moreover, the above discussion has shown the desirability of using a crystal-controlled oscillator with an output reduced by binary dividers.

However, the generally available crystals only provide a limited number of frequencies within the desired range. Thus, controllers employing the two different types of variable divider and only generally available crystals should have the ability of using the same casette. They should, nonetheless, accurately deliver the desired quantity of fluid over an extended period of time.

The deliverable volume of the casette, moreover, must meet other restrictions. Thus, it cannot have such a large volume that the flow stops for extended periods of time. If fluid does not regularly pass through the needle within the patient's vein, clotting can occur around it and prevent passage of the further intravenous fluid.

Furthermore, a casette with an excessively large volume would require a large hydrostatic head to force fluid into and out of it.

Yet, the casette's metering chamber should have as large a size as practical to limit the number of cycles required to deliver the desired volume. If the chamber had a particularly small size, the controller would have to undergo a large number of operations and consume the limited power within a battery.

To meet the above general criteria, the size of the casette must fall within the range of 0.2 to 0.4 ml. Providing it with a specific volume of 0.29 ml. would allow it to perform adequately under most circumstances. More exactly, a volume of 0.2898 ml. would produce minimum deviations from the desired volumes using either of the two types of controllers discussed above.

The valves of the casette must remain open long enough to allow the fluid to flow into or out of it, as appropriate. Yet, the controller must have a sufficiently high frequency of pulses to provide it with the flexibility it needs to maintain a relatively even flow of fluid over an extended period of time. The frequency of pulses that it can utilize must also provide the flexibility required to allow for the delivery of the desired amount of intravenous solution over extended periods of time.

Consequently, the regulator on the controller should include a pulsing section providing electronic pulses at a predetermined first frequency. To provide the required time intervals during which each of the valves of the casette remains open, the regulator also includes a pulse absorbing device coupled to the pulser. Upon the receipt of the first predetermined number of the electronic pulses produced by the pulser, the absorber produces a second predetermined number of its own output pulses. The number of these output pulses should not, however, exceed half of the electronic pulses it received. Moreover, after producing a first of its output pulses, it should not produce a second until it has received two of the pulser's electronic pulses subsequent to the start of the first output pulse.

The higher frequency of the electronic pulses from the pulsing device provides the circuit with the flexibility required to provide variable but accurate amounts of fluid to the patient. The restrictions on the pulse absorbing device produce the time periods required for the casette to fill and empty properly.

To take advantage of the pulses produced both by the pulsing means and the pulse absorber, the regulator should also include a responding device coupled to both of these components. Upon receiving one of the output pulses, the responding device will cause the moving means to place the first or inlet, valve member in a position which it opens the inlet. At that time, the outlet valve member should close. This configuration of the valves allows the casette to fill.

When the responding device then receives one of the pulser's electronic pulses not occurring during the absorber's output pulse, it can return the valving members to their prior positions. Specifically, the first valving member goes to its second position and closes the inlet. The second, or outlet valve member, moves to its third position which opens the outlet. As a result, fluid from the casette flows to the patient.

Generally, the absorber's output pulses may have the same duration as the electronic devices from the pulser. Then, achieving the length of time required for the casette to fill requires the careful placement of each of the absorber's output pulses. Specifically, each pulse may begin shortly after the termination of a electronic pulse. This would cause it to remain alive at the start of the succeeding electronic pulse. Only the second succeeding electronic pulse could cause the responding device to close the inlet valve of the casette. With this careful placement, the casette would have a cycle and a half of the pulser's pulse train to fill. Thus, if each cycle of the pulsing device lasted one second, the casette could have 1.5 seconds to fill.

However, the moving means does not move the valving members during the entire time that the casette either fills or empties. In fact, the moving means effects motion only during very brief intervals at the beginning of each portion of the operational cycle. Consequently, the moving means does not require a supply of power during most of the operational cycle.

Thus, to save electrical energy, the controller's regulator may include timing means to produce changes in its electronic state after the passage of predetermined time intervals. The responding device then couples to the timing means, a source of electric current, and to the moving means.

When the timing means produces a change in its electronic state, the responding device provides electric current to the moving means for a brief period of time. These time periods just suffice to effect motion of the inlet or the outlet valving members to move between their two positions. The length of time that the moving means receives current, to achieve the desired savings, must remain shorter than any of the time intervals between electronic-state changes produced by the timing means.

BRIEF DESCRIPTION OF THE FIGURES

FIG. 4 gives a timing diagram for pulses occurring at various points in the circuit of FIG. 3.

DETAILED DESCRIPTION

Figure 1:
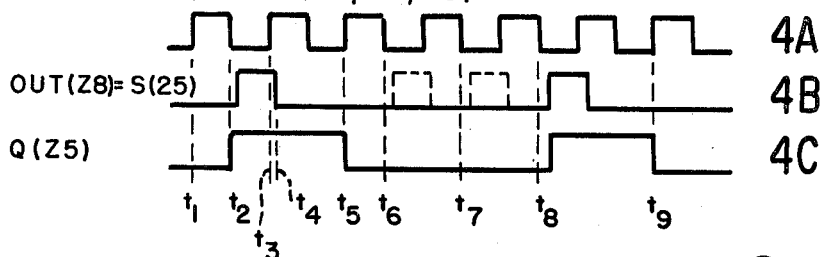
FIG. 1 shows, partly in cross section, a casette having an elastomeric membrane sandwiched between two sections of plastic.
Figure 1:
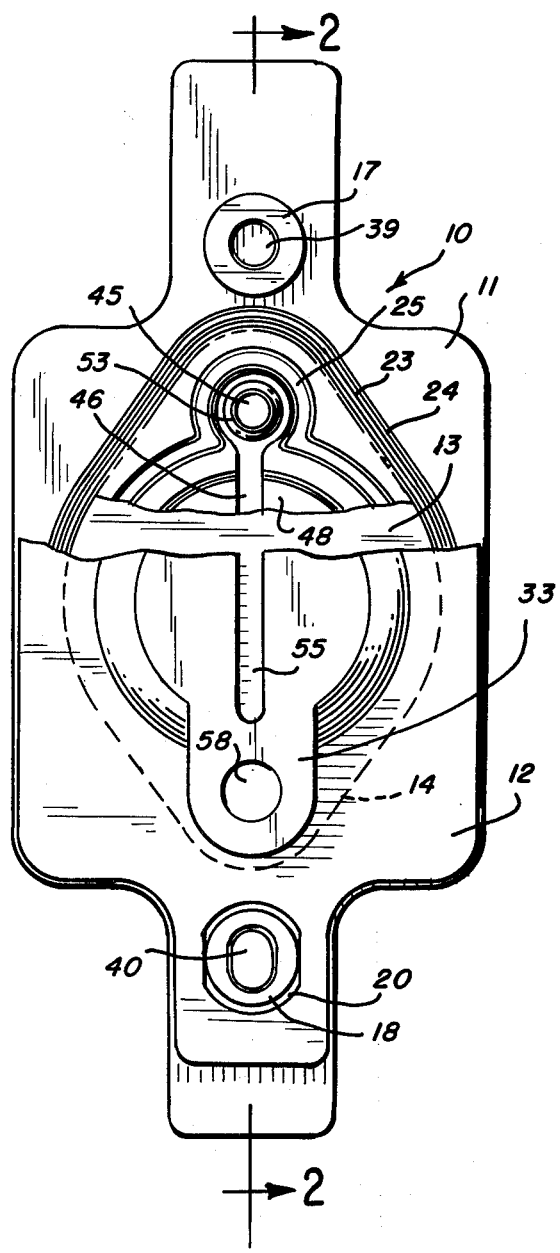

The casette shown generally at 10 in FIG. 1 includes the base section of plastic 11 and the cover plastic slip 12. Sandwiched between them appears the elastomeric membrane 13. The line 14 indicates the periphery of the membrane 13 where it does not itself appear.

The circular protuberances 17 and 18 in the base section of plastic 11 fit into the openings 19 (seen in FIG. 2) and 20. When the protuberances 17 and 18 fit into the openings 19 and 20, respectively, they properly align the two sections of plastic relative to each other. The opening 20 has an elongated shape towards the direction of the other opening 19. This allows some manufacturing tolerance between the exact location of the protuberance 18 relative to the opening 20. The snug fit of the opening 19 around the protuberance 17 assures the proper alignment of the two sections of plastic.

To fuse the two plastic sections 11 and 12 together, the former receives ultrasonic waves. This melts the ridge 23 and fuses the two sections together. The base plastic section 11 also includes the shallow well 24 which provides any excess melted plastic from the ridge 23 a depository where it will not interfere with the adjoining of the two sections.

The ultrasonic waves, applied to the base section of plastic 11, could cause the elastomeric membrane 13 to move about and loose its proper orientation. The cover slip of plastic 12 includes a ridge with a sharp edge fitting into the well 25 of the base plastic section 11. The ridge and the well 25 simply hold the membrane 13 in place during the application of the ultrasonic waves.

Figure 2:
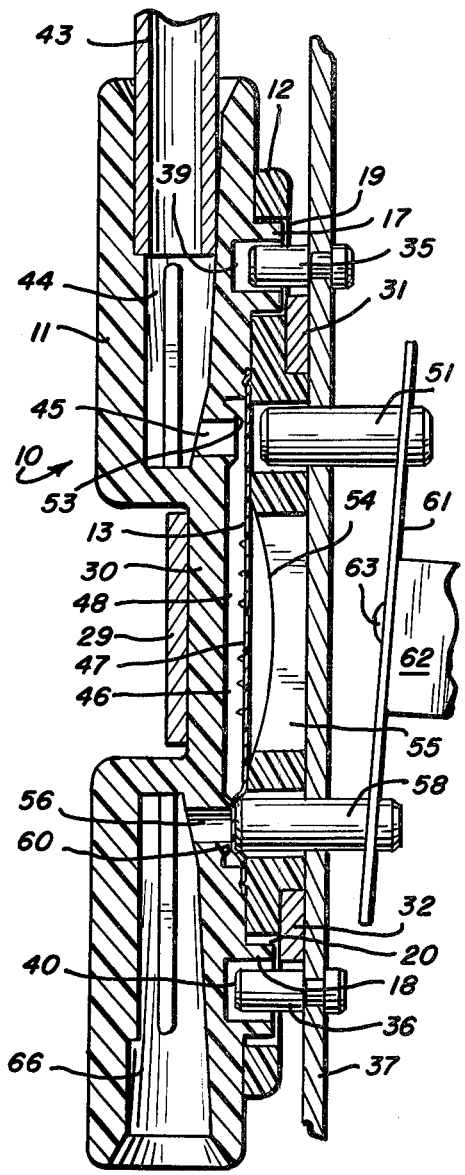
FIG. 2 gives a cross-sectional view along the line 2—2 of the casette of FIG. 1 engaged with the portion of a controller which operates its valves.

To grasp onto the casette 10, the controller includes the plate 29 which fits against the back 30 of the casette 10 in FIG. 2. The controller also has the arms 31 and 32 which fit on either side of the protuberance 33 formed in the cover section of plastic 12. The back plate 29 and the arms 31 and 32 form part of a unitary casette holder. It moves from left to right in FIG. 2. As it moves to the right, it allows the alignment pins 35 and 36 on the plate 37 of the controller to enter the openings 39 and 40 formed in the protuberances 17 and 18 of the casette 10. Again, the opening 40 has an elongated appearance while the opening 39 has a circular shape. This allows some manufacturing tolerance for the former while the close fit of the latter around the alignment pin 35 of the controller properly aligns the two components in the system.

In operation, the plastic tube 43 connects to the bottle of intravenous solution. The fluid from the tube 43 enters the inlet channel 44 and passes to the inlet opening 45. At the beginning of the controller's operational cycle, the casette and the controller would have the configuration shown in FIG. 2. There, the membrane 13 lies flatly against the base plastic section except over the groove 46 which assures a flow path for fluid through the casette when not under the controller's guidance.

In FIG. 2, no fluid has entered the metering chamber 47 formed between the membrane 13 and the flat plastic surface 48 (seen more clearly in FIG. 1). However, the inlet valve member 51 has retracted slightly from the valve face 53 of the inlet 45. This allows fluid from the intravenous bottle to enter the metering chamber 47 and force the elastomeric membrane 13 away from the plastic surface 48. As the fluid flows into the metering chamber 48, the elastomeric membrane 13 expands until it contacts the concave surface 54 formed in the cover plastic slip 12. The surface 54 limits the expansion of the membrane 13 and thus provides the metering chamber 47 with a predetermined known maximum volume. The slot 55 through the cover plastic slip 12 disipates any partial air pressure developed from the expansion or contraction of the membrane 13 as the casette fills or empties, respectively.

As the fluid enters the metering chamber 47, it cannot egress through the outlet 56. That results since the outlet valve member 58, which passes through the opening 59 in the cover plastic section 12, has forced the membrane 13 against the outlet valve face 60. As a result, the membrane 13 effectively blockades the passage of any fluid from the casette 10.

After the metering chamber 47 has filled with fluid, the second portion of the operating cycle may commence. To proceed to this phase of operation, the spring link 61, which connects to the valve members 51 and 58, changes its orientation. This task represents the function of the controller. To accomplish it, the connecting link 61 has the side leg 62 which couples to the rockerarm armature of an electromagnet. The screw 63 maintains this connection.

Specifically, to begin the second phase of operation, the link 61 pivots in a counterclockwise direction in FIG. 2. The springiness or resiliency of the link 61 allows the inlet valve member 51 to place the membrane 13 into contact with the inlet valve face 53 before the outlet 56 can open. This prevents the uncontrolled flow of fluid directly through the casette 10. Once the inlet 45 closes, the link 61 retracts the outlet valve 58 from the outlet 56. As the outlet valve 58 moves, it allows the membrane 13 to pull away from the outlet valve face 60. Fluid then passes out through the outlet 56 and the outlet channel 66 and to the usual tubing to the patient. After the metering chamber 47 has emptied, the link 61 pivots in the clockwise direction in FIG. 2 to first close the outlet 56 and then open the inlet 45 to commence a new cycle of operation.

Figure 3:
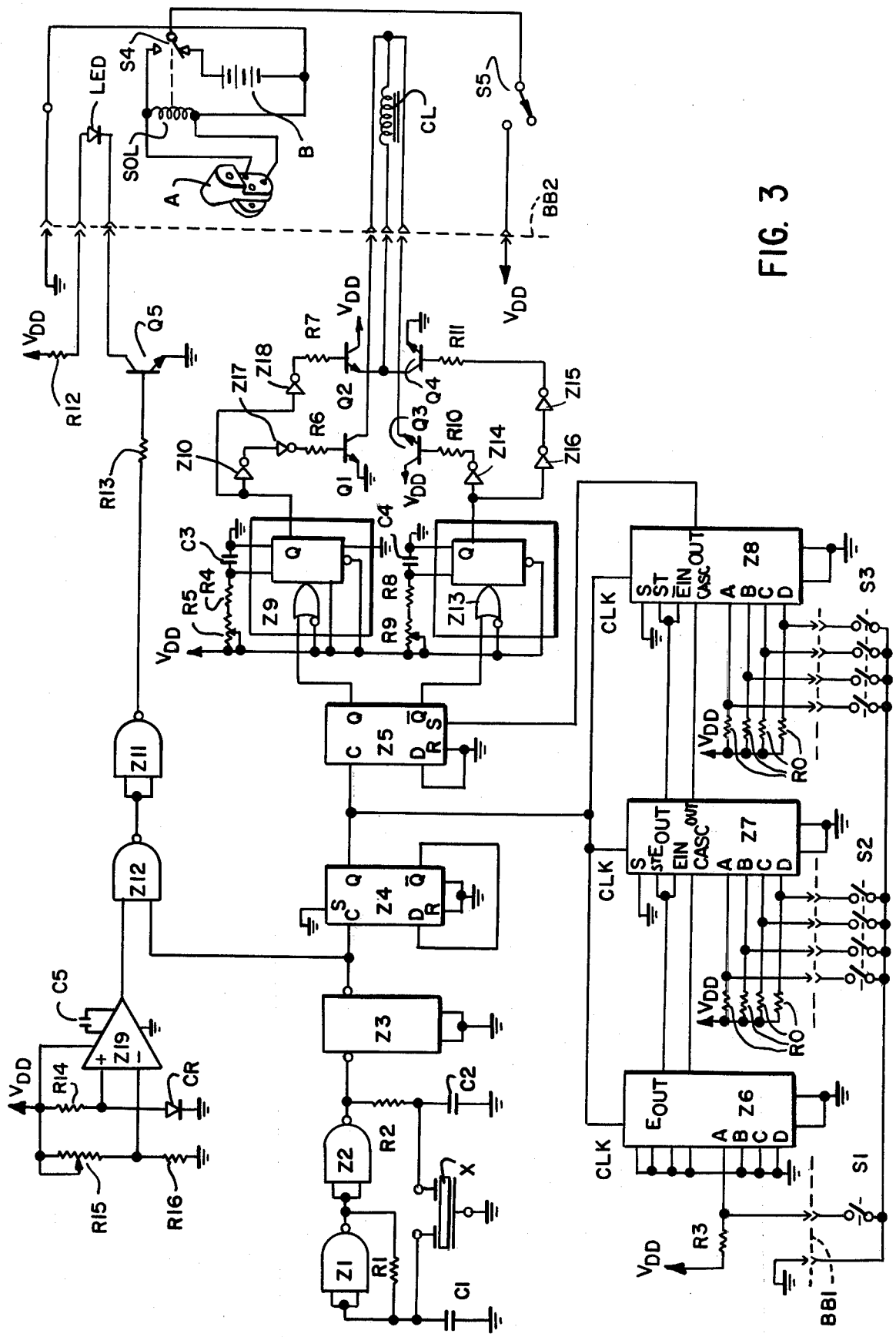
FIG. 3 gives an electronic circuit which regulates the operation of the controller.

Controlling the motion of the valving members 51 and 58 represents the function of the circuit diagrammed in FIG. 3. Specifically, the coil CL forms part of the electromagnet to the armature of which the spring link 61 connects. Current passing from left to right through the coil CL results in the spring link 61 rotating to the clockwise position of FIG. 2. That allows the inlet 45 to open and the metering chamber 47 to fill.

When the current passes through the coil CL from right to left, the spring link 61 rotates in the counterclockwise direction. That closes the inlet, opens the outlet, and permits the fluid from the metering chamber 47 to pass to the patient.

To provide the fundamental controlling pulses, FIG. 3 includes the oscillating circuit composed of the crystal X, the capacitors C1 and C2, the resistors R1 and R2, and the NAND gates Z1 and Z2. Operating below their saturation levels, the NAND gate Z1 and Z2 function in an analog fashion to provide the gain and, with the remaining components, the 360° phase shift required for oscillation. The crystal X controls the frequency of that oscillation.

The circuit segment with these components is standard and receives a description in the catalog of manufacturer of the crystal X. Readily available frequencies for the crystal X include 100 KHz., 76.8 KHz., 60 KHz., 40.961 KHz., 38.4 KHz., 32.768 KHz., 31.5 KHz., 30.72 KHz., 20.48 KHz., 19.2 KHz., 18.641 KHz., 16.384 KHz., 16 KHz., 15.36 KHz., 12.8 KHz., and 10 KHz.

The oscillator shown in the figure produces pulses at a frequency of 31.5 KHz. It passes this frequency to the divider Z3 which divides it by the factor of 16,384. The resulting square-wave pulse train has a frequency of 1.9226074 Hz. and travels to the flip-flop Z4 which divides again by two. The output pulse frequency of 0.9613037 Hz. passes to the C input of the D-type flip-flop Z5 as well as to the clock input CLK of the cascaded binary rate multipliers Z6, Z7 and Z8. The rate multipliers Z6 to Z8 receive information from the thumb wheel switches S1 to S3, respectfully. The busbar BB1 connects the switches S1 to S3 to the circuit board with the multipliers Z6 to Z8.

The switch S1 has only two positions. It can only provide the numbers 0 or 1 to the multiplier Z6. When closed, it provides a ground potential to the A input of the multiplier Z6. This represents the selected number 0. When open, the switch S1 isolates the A input of the multiplier Z6 from ground. Consequently, the circuit potential $V_{DD}$ passes across the resistor R3 to the A input. This signifies the selected number 1.

Moreover, the switch S1 and the multiplier Z6 represent the left most components of the three multipliers Z6 to Z8 and the switches S1 to S3. Consequently, it provides the hundreds input of the cascaded multipliers. Thus, opening the switch S1 corresponds to the integer 1 but actually represents the number 100.

The rate multipliers Z7 and Z8 have the four-fold switches S2 and S3. Each of these switches allows the selection of any integer from 0 to 9 for the multipliers Z7 and Z8. The switch S2 provides the tens input to the three-digit number formed from the three switches S1 to S3 while the switch S3 provides the ones input.

The circuit shows the three multipliers Z6 to Z8 coupled together in a cascaded fashion. Operated in this mode, they provide a number of pulses at the OUT output of the multiplier Z8. The exact number of such output pulses depends upon the number of input pulses appearing at their CLK inputs and the integers selected on the switches S1 to S3. For each 1000 pulses appearing at the CLK inputs of these multipliers, the OUT output of the multiplier Z8 will provide a quantity of pulses equal to the three-digit number selected on the switches S1 to S3. With the number 165, selected, for example, the multiplier Z8 will provide 165 output pulses for each 1000 input pulses received by the multipliers Z6 to Z8.

The output pulses provided by the multiplier Z8 have several important characteristics. They do not fall into a regular pulse train having equal time durations in the higher and lower voltage levels. Rather, it produces positive pulses equal in duration to the positive pulses received at the CLK inputs to the multipliers Z6 to Z8. As a result, the lower voltage level at the OUT output of the multiplier Z8 may last several times longer the positive pulses from the OUT output.

Furthermore, the binary rate multipliers Z6 to Z8 invert their outputs. Stated in other terms, a positive output pulse will commence immediately after the end of the positive input pulse which produced it. As discussed in further detail with regards to FIG. 4, the output pulse from the multiplier Z8 occurs basically during a time when the input pulse train at the CLK input provides the lower voltage level.

Since the output pulses have the same duration as and begin upon the termination of an input pulse, they, for most numbers dialed on the switches S1 to S3, do not occur regularly. This is, they do not have regular spacings between them. The time intervals between the output pulses depends upon the number that must appear from the binary divider Z8 for each 1000 input pulses.

The OUT output of the divider Z8 couples to the S, or "SET", input of the flip-flop Z5. As mentioned above, the Q output of the flip-flop Z4 couples to the C input of the same flip-flop Z5. The flip-flop Z5 and the characteristics of the pulses produced by the multiplier Z8 provide the coordination that allows sufficient time for the casette to empty and fill.

Typically, the controller maintains the inlet valve of the casette closed and the outlet valve open. To reverse that requires an output pulse from the binary rate multiplier Z8. FIG. 4 gives a timing sequence showing the operation of the flip-flop Z5. FIG. 4A shows the pulse train provided by the Q output of the flip-flop Z4 which passes to the C input of the flip-flop C5. FIG. 4B gives various pulses produced, under different circumstances, from the OUT output of the binary rate multiplier Z8. FIG. 4C, showing the Q output of the flip-flop of Z5, illustrates the behavior of that component in response to its inputs.

Beginning a cycle of operation requires a pulse from the Q output of the flip-flop Z4 to the C input of the flip-flop Z5. This pulse appears in FIG. 4A at t1. To initiate a cycle, this pulse must then produce an output pulse from the divider Z8. This output pulse occurs at about the time t2 in FIG 4B. Specifically, the beginning of the output pulse occurs slightly after the time t2, which represents the end of the pulse from the flip-flop Z4. The slight difference in times reflects the time required for an electronic component to react.

The pulse from the output of the binary divider Z8, shown in FIG. 4B, travels to the S input of the flip-flop Z5, shown in FIG. 3. This causes the Q output of the flip-flop Z5 to immediately become positive, which it does at about the time t2. The Q output of the flip-flop Z5 becoming positive, as discussed below, causes a pulse of current to pass to the coil CL. It, thus, opens the casette's inlet and closes the outlet to begin a cycle of operation.

To subsequently close the casette's inlet, open its outlet, and allow fluid to flow to the patient requires that the $\overline{Q}$ output of Z5 become positive. This can only happen when its Q output goes to ZERO. That, however, will occur only upon the receipt of a pulse at the C input of the flip-flop Z5. This would pass the ZERO input at the D, or "data", input of the flip-flop Z5 to its Q output. However, a pulse at the D input to the flip-flop Z5 cannot effectuate this transition at the Q output as long as a positive pulse remains at the S input; the positive voltage level at the S input predominates over the clocking of the ZERO voltage level at the D input.

Accordingly, the next pulse at the C input of the flip-flop Z5 after the start of the Q output pulse at t2 begins at the time t3. However, at t3, the S input of the flip-flop Z5 remains positive for an additional short period of time because of the slight lag of the rate multipliers Z6 to Z8 due to their response time.

At the time t4, however, the S input to the flip-flop Z5 does return to ZERO. However, that comes too late since the flip-flop can only respond to a C input pulse at the beginning of such a pulse. Thus, the Q output of the flip-flop Z5 remains positive through the times t3 and t4 as shown.

At the time t4, the multiplier Z8 has its OUT output returning to ZERO. With it, the S input to the flip-flop Z5 goes to ZERO.

At the subsequent time t5, the next clock pulse appears at the C input to the flip-flop Z5. This causes the ZERO at the D input of a flip-flop Z5 to force the Q output to ZERO. At that point, the $\overline{Q}$ output of the flip-flop Z5 goes positive. As discussed below, $\overline{Q}$ going positive causes current to flow in the coil CL in the direction that will close the inlet to the casette and open its outlet.

Thus, the input to the casette remains open from the time t2 until the time t5. That amounts to slightly less than 1.5 seconds. This provides adequate time for the casette to fill.

The pulse at the Q output of the flip-flop Z4 occurring at the time t5 could cause the binary rate multiplier Z8 to provide a further positive output pulse to the S input of the flip-flop Z5. That pulse, indicated in phantom in FIG. 4B, would occur at the time t6. However, such a pulse appearing at t6 at the S input of the flip-flop Z5 would immediately cause its Q output to go positive. That would reopen the casette's inlet and close the outlet.

However, the outlet would have remained open only during the time from t5 to t6. This would only approximately allow 0.5 seconds for the fluid to flow out of the casette. This half of a second may not suffice to allow all the fluid to leave the casette. Consequently, the binary rate multiplier Z6 to Z8 should not allow a pulse to pass out of it until the casette has had approximately 1.5 seconds to empty. Accordingly, the next pulse that should even possibly commence a further cycle of operation should occur no earlier than at the time t7. That would allow the casette about 1.5 seconds to empty.

Typically, however, the patient should not receive more than about 200 ml. of solution per hour. With a casette having a volume of 0.29 ml. and the frequency of the pulses shown in FIG. 4A, the next positive pulse appearing at the S input of the flip-flop Z5 need not occur until the time t8. This would then cause the succeeding cycle of operation to begin at that time as shown by FIG. 4C, which gives the state of the Q outlet of the flip-flop Z5.

In other words, the OUT output of the rate multiplier Z8 need only provide one output pulse for every five input pulses received from the Q output of the flip-flop Z4. Accordingly, the operational cycle of the casette could repeat itself once for every 4.5 seconds. Even at this rate, though, the casette could deliver approximately 230 ml. of solution per hour. To achieve the upper limit of 200 ml. per hour, some cycles have to commence on the sixth, as opposed to the fifth, pulse after the commencement of the prior cycle. For lower flow rates, the commencement of the cycles may even wait longer than six clock pulses after the commencement of the prior cycle.

Returning to the flip-flop Z5, when its Q output goes positive to open the casette's inlet, it provides a positive pulse to the monostable multivibrator Z9. The multivibrator Z9, in response, provides a short positive pulse at its Q output. The length of this pulse depends upon the magnitudes of the resistors R4 and R5 and the capacitor C3. The pulse need last only long enough for current to flow in the coil CL for a sufficient time to move the armature of its electromagnet. It does not have to flow while the valve members rest in any one position.

In other words, the current in the coil CL does not maintain the valve members in a position; the current only moves them between their different positions. Thus, the coil CL only needs current for a very brief period of time. Certainly, it needs current for less than one half or even one tenth the duration of positive pulses from the flip-flop Z4 or Z5 or the multiplier Z8. Specifically, 20 to 25 msec. suffices. This compares to the period of time of 0.5 sec., or 500 msec., that the casette's inlet remains open. As discussed above, the outlet of the casette remains open for even longer periods of time.

To achieve the exact desired length of time for the current to flow, the value of the resistor R5 may vary. Thus, after the construction of the circuit, adjusting the resistor R5 will produce the appropriate pulse from the Q output of the monostable multivibrator Z9. This allows the appropriate current flow through the coil CL to move the valving members as desired.

In operation, the pulse from the Q output of the multivibrator Z9 passes through the inverters Z10 and Z17 and the resistor R6 to turn on the transitor Q1. The pulse also passes through the inverter Z18 and the resistor R7 to turn on the transistor Q2. With the transistors Q1 and Q2 turned on, current may flow from the potential source $V_{DD}$ through the transistor Q2 and the coil CL and back through the transistor Q1 to ground. At the end of the pulse from the Q output of the multivibrator Z9, the transistors Q1 and Q2 turn off and prevent the further flow of current through this path.

The inverters Z10 to Z17 and Z18 have two functions. First, they act as buffers between the multivibrator Z9 and the transitors Q1 and Q2. Accordingly, they provide sufficient current to the transistors to maintain them in their conducting state. This becomes particularly important since transistors Q1 and Q2, the coil CL, and the transistors Q3 and Q4 form a bridge circuit. The currents experienced by the bases of the transistors Q1 and Q2 could differ. They would, consequently, receive different amounts of current. One might not receive enough to conduct. The buffering provided by the inverters Z10 Z17 and Z18 prevents this occurrance and supplies sufficient current to both the transitors Q1 and Q2. Additionally, the inverter Z17 provides a voltage and current of the correct polarity to cause the transitor Q1 to conduct.

When the casette has filled, the controller must close the inlet and open the outlet to allow the aliquot of fluid to flow to the patient. This results when the $\overline{Q}$ output of the flip-flop Z5 goes positive, which it does at the times t5 and t9 in FIG. 4C. This positive pulse travels to the monostable multivibrator Z13. As with the multivibrator Z9, the multivibrator Z13 provides a pulse at its Q output of sufficient duration to allow the current in the coil CL to reorient the valving members. The length of the pulse at the Q output of the multivibrator Z13, of course, depends upon the magnitudes of the resistors R8 and R9 and the capacitor C4. Adjusting the resistor R9 achieves pulses of the desired duration. They generally have the same lengths as the pulses from the multivibrator Z9.

This brief output pulse from the multivibrator Z13 then travels through the inverter Z14 and the resistor R10 to turn on the transistor Q3 and through the inverters Z15 and Z16 and the resistor R11 to turn on the transistor Q4. This allows current to flow from the potential source $V_{DD}$, to the transistor Q3 and the coil CL, and back through the transistor Q4 to ground. However, the current flowing along this path passes through the coil CL in the opposite direction than current provided when the transitors Q1 and Q2 conduct. Thus, it would force the armature of the electromagnet to move in the opposite direction and open the casette's outlet while closing its inlet. Again, the inverters Z13 to Z15 serve a buffering function while assuring the correct polarity for the transistors Q3 and Q4.

The power supply for the circuit of FIG. 3 appears on its right-hand side. As shown there, an a.c. adapter A may connect to the usual A.C. electric outlets of a building. It then filters and rectifies the voltage to provide a d.c. voltage of the desired magnitude, particularly nine volts. This potential would first appear across the solenoid SOL which would force the switch S4 against its upper contact. As a result, the voltage provided by the adapter A would appear between ground and the voltage supply connection $V_{DD}$ at the bus-bar BB2. The on-off switch S5 would, of course, have to move to its "on", or upper position to energize the circuit.

Should the adapter A not provide power to the solenoid SOL, the switch S4 would drop to its lower contact and connect to the battery B. This would allow the circuit to operate on the energy provided by the battery B.

Should the battery B as well as the adapter A not provide sufficient current, the circuit includes the light emitting diode LED. This warns the attendant that the controller requires a new source of electrical energy.

The remainder of the circuit concerns the operation of the LED when the battery B wears down. For the LED to turn on, the current must flow from the potential source $V_{DD}$ through the resistor R12, the LED itself, and the transistor Q5 to ground. That requires the transistor Q5 to conduct, at least to some degree. For that to happen, its base must have a positive applied voltage. However, the base of the transistor Q1 receives its voltage through the resistor R13 from the NAND gate Z11. With its two inputs coupled together, the NAND gate Z11 simply acts as an inverter. Thus, to have a positive output, it must receive a ZERO input from the NAND gate Z12.

In turn, the NAND gate Z12 can produce a ZERO output when it has both of its lower and its upper inputs in the positive state. The lower input, in turn, couples to the output of the divider Z3. Consequently, the lower input to the NAND gate Z12 pulses between ZERO and the positive state with a regularity assured by the divider Z3. Once each cycle, in other words, the lower input to the NAND gate Z12 goes to the positive state. During the other half of the cycle, the lower input goes to ZERO and prevents the LED from lighting. The connection of the lower input to the NAND gate Z12 to the output of the divider Z3 simply causes the LED to flicker when the voltage falls below a predetermined value. By itself, the output of the divider Z3 cannot cause the LED to turn on.

The flickering caused by the coupling of the NAND gate Z12 to the divider Z3 has two purposes. Primarily, it produces a visual effect from the light LED which will attract the attention of the attendant to warn him of the shrinking power supply. Incidentally, it turns off the light LED for half of each cycle and, thus, conserves some of the remaining energy.

The other condition for the NAND gate Z12 to allow the light LED to turn on requires that its upper input also occupy the positive state. This in turn requires a positive output from the linear amplifier Z19. With its connection to the voltage supply $V_{DD}$ and the capacitor C5, the amplifier Z19 acts as a comparator.

The linear amplifier Z19 does not include any capacitance. It could, as a result, possibly oscillate. The capacitor C5 provies the capacitance required to prevent the possibility of this undesired oscillation.

When the voltage appearing at the positive, or "+", input of the linear amplifier Z19 exceeds that at its negative, or "−", input, its output goes to the positive state. This would then cause the light LED to turn on.

However, the voltage appearing at the "+" input of the linear amplifier Z19 results from the applied voltage $V_{DD}$ reduced by the potential drop across the resistor R14. Since the supply voltage $V_{DD}$ remains positive, relative to ground, the diode CR normally remains in its conducting state. This would allow the voltage at the "+" input to the amplifier Z19 to very closely approximate ground with substantially all of the potential drop from the supply voltage $V_{DD}$ to ground occurring across the resistor R14. However, a voltage drop does occur across the diode CR even when it conducts. This amounts to approximately 0.4 to 0.5 volt. This then represents the voltage appearing at the "+" input of the amplifier Z19. The voltage drop across the diode CR, however, can vary slightly as the battery B wears down.

The voltage appearing at the "−" input of the amplifier Z19 is produced at the midpoint of the voltage divider composed of the resistors R15 and R16. In other words, the potential at the "−" input represents a fraction of the voltage drop from the supply voltage $V_{DD}$ to ground. The exact fraction, of course, depends upon the magnitudes of the resistors R15 and R16.

With a fresh battery B producing its full output, for example 9 volts, the voltage at the "−" input of the amplifier Z19 exceeds that at its "+" input. Consequently, the amplifier Z19 provides a negative output to the upper input of the NAND gate Z12. This keeps the light LED from turning on. It also represents the required result since the battery B possesses its fully supply voltage $V_{DD}$.

As the battery B wears down, the supply voltage $V_{DD}$ will drop. As it does, the voltage at the "−" input of the amplifier Z13, which simply represents the constant fraction of the supply voltage $V_{DD}$, also diminishes. At some point it will fall below the voltage appearing at the "+" input. This change in the relative magnitudes of the "+" and the "−" inputs will cause the output of the amplifier Z19 to jump to its positive state. This forces the output from the NAND gate Z12 to go positive during the half cycles that it receives positive inputs from the divider Z3. During these times, the output of the NAND gate Z12 goes to ZERO and the light LED turns on. Thus, when the battery B supplies a insufficient voltage supply $V_{DD}$, the light LED flickers on, as desired.

As mentioned above, the potential at the "+" input of the linear amplifier Z19 will vary slightly as the voltage $V_{DD}$ supplied by the battery B starts to drop. However, the resister R14 can vary in order to allow the calibration of the exact supply voltage $V_{DD}$ at which the light LED turns on. The resistor consequently receives an original adjustment upon its initial manufacture. The desired point at which the light should flicker on, for example 6.5 volts, will be applied as the supply voltage $V_{DD}$. The manufacturer will then adjust the variable resistor R14 until the LED barely turns on. In future operation, then, whenever the supply voltage $V_{DD}$ drops below the predetermined point, the LED will flicker to warn the attendant.

The circuit shown in FIG. 3 includes the crystal controlled oscillator. Using the crystal X eliminates the need to calibrate the frequency with capacitors. The crystal X also provides a relatively low frequency. This avoids a high degree of division in order to achieve an operational frequency. Also the high frequencies of equipment around the hospital, such as a diathermy machine, could interfere with electrical components that could respond to these high frequencies.

Furthermore, all of the electronic components included in the circuit have a composition of CMOS. This accomplishes two objectives. First, they remain insensitive to the stray high frequencies mentioned above. Secondly, they consume minimal power and thus extend the life of a battery used to power the circuit.

A cassette with a deliverable volume of 0.2898147 ml. has important advantages. A circuit employing a crystal of 100,000 Hz. and division by only a positive integral power of two and responding to each pulse produced by the divider will, with this casette, deliver exactly 199 ml./hr. This appears from the following equation:

$$\frac{(.2898147 \text{ ml./cy.}) (10^5 \text{ cy./sec.}) (3600 \text{ sec./hr.})}{2^{19}} = 199 \text{ ml./hr.} \quad (1)$$

This equation suggests the division of the crystal frequency by the 19th power of two which equals 524,288.

However, the circuit of FIG. 3 employs the binary rate multipliers Z6 to Z8. The highest number which the attendant can dial onto the switches S1 to S3 is 199 since the patient should not receive substantially more than that number of millilters of solution per hour. Consequently, the binary multipliers Z6 to Z8 can only allow 199 cycles of operation for each 1000 pulses produced by the dividers Z3 and Z4. Moreover, the circuit employs a crystal of 31.5 KHz. Under these conditions, the circuit, still using a casette size of 0.2898147 ml., will provide an output per hour of 199.5899 ml./hr. according to the following equation:

$$\frac{(.2898147 \text{ ml./cy.})(31,500 \text{ cy./sec.})(3600 \text{ sec./hr.})}{(1000/199) \, 2^{15}} = 199.5899 \text{ ml.} \quad (2)$$

This gives an error of 0.296%. Thus the same casette size will give exactly the desired 199 ml./hr. in a circuit using a crystal controlled oscillator with a frequency of 100,000 Hz., binary rate division, and the utilization of each pulse produced by the dividers. The same casette size gives a error less than 0.3% using binary rate multipliers connected to selection switches an oscillator frequency of 31,500 Hz., and only binary division of the oscillator output. And, it falls within the desired range of 0.2 to 0.4 ml. Thus, generally speaking, the cassette size of 0.29 ml. or, more accurately, 0.2898 ml. would appear to have particular benefits for use with a controller, especially one using a crystal controlled oscillator.

As mentioned above, a patient should generally receive I.V. solution within the range of 18 to 199 ml./hr. Accordingly, when using this casette, the flip-flop Z5 must receive at least one pulse per minute from the multiplier Z8 to provide the lower limit, If the multiplier Z8, on the other hand, provided more than one pulse per second, the upper limit would be exceeded.

Components giving satisfactory performance in the circuit of FIG. 3 appear in the Table.

TABLE

| Component | Components Used in FIG. 3 Identification |
|---|---|
| B | 9V. Lithium SRL-5476 |
| C1,C2 | 5 pF |
| C3,C4 | .1 μF |
| C5 | 100 pF |
| CL | 2072 turns of #33 copper wire |
| CR | IN914 |
| LED | MV 5053 |
| Q1,Q4,Q5 | 2N3301 |
| Q2,Q3 | 2N4032 |
| R0,R3 | 150 KΩ |
| R1 | 330 KΩ |
| R2 | 100 KΩ |
| R4,R8 | 750 KΩ |
| R5,R9 | 500 KΩ |
| R6,R7,R10,R11 | 470 KΩ |
| R12 | 220 KΩ |
| R13 | 5.1 KΩ |
| R14 | 33 KΩ |
| R15 | 100 KΩ |
| R16 | 6.8 KΩ |
| Z1,Z2,Z11,Z12 | MC 14011 |
| Z3 | MC 14020 BCP |
| Z4,Z5 | MC 14013 BCP |
| Z6,Z8 | MC 14527 BCP |
| Z9,Z13 | MC 14528 BCP |
| Z10,Z12,Z14,Z16 | MC 14049 BCP |
| X | SX-1H 31.5 Statec Crystal |

Accordingly, what is claimed is:

1. In a controller for use with a casette having:
   (a) metering means for holding a predetermined volume of a fluid;
   (b) closable inlet means, in fluid communication with said metering means, for permitting the flow of a fluid into said metering means; and
   (c) closable outlet means, in fluid communication with said metering means, for permitting the flow of a fluid out of said metering means, said controlling having:
   (a) first member means, movable between a first position and a second position for, when in said second position, closing said inlet means;
   (b) second member means, movable between a third position and a fourth position for, when in said fourth position, closing said outlet means; and
   (c) moving means coupled to said first member means and said second member means for moving said first member means between said first and second positions and said second member means between said third and fourth positions; and
   (d) regulating means, coupled to said moving means, for controlling the operation of said moving means, the improvement wherein said regulating means comprises:
   (A) crystal controlled oscillating means for producing digital pulses at a predetermined first frequency of less than 1 MHz;
   (B) digital gate means coupled to said oscillating means for, upon the receipt of pulses at said first frequency from said oscillating means, providing output pulses at a second frequency which is less than half of said first frequency; and
   (C) responding means coupled to said gate means and to said moving means for, upon the receipt of an output pulse from said gate means, causing said moving means to alternatingly move said first member means between said first and second positions and move said second member means between said third and fourth positions; said digital gate means including (1) binary divider means coupled to said oscillating means, for producing, at regular intervals, intermediate pulses equal in number to the number of electronic pulses divided by a positive integral power of two, and (2) variable rate-divider means coupled to said binary divider means, for producing said second predetermined number of said output pulses with said second predetermined number being less than one third the number of said intermediate pulses, and wherein said responding means receives said intermediate pulses and said output pulses and, upon receipt of an output pulse, causing said moving means either (i) to move said first member means into said second position and said second member means into said third position or (ii) to move said first member means into said first position and said second member means into said fourth position, and upon the receipt of an intermediate pulse, causes said moving means to move said first and second member means in the opposite direction than upon the receipt of an output pulse.

2. The improvement of claim 1 wherein said first frequency is selected from the group consisting of 100,000 Hz., 76,800 Hz., 60,000 Hz., 40,960 Hz., 38,400 Hz., 32,768 Hz., 31,500 Hz., 30,720 Hz., 20,480 Hz., 19,200 Hz., 18,641 Hz., 16,384 Hz., 16,000 Hz., 15,360 Hz., 12,800 Hz., 10,000 Hz.

3. The improvement of claim 2 wherein said oscillating means and said responding means each include electronic logic components, with all of said electronic logic components being CMOS components.

4. The improvement of claim 3 wherein said controller is used with a casette in which said metering chamber has a deliverable volume of 0.2898 ml.

5. The improvement of claim 2 wherein said responding means couples to said binary divider means and to said variable rate divider means and, upon a receipt of an output pulse, moves said first members means into said second position and said second member means into said third position and, upon the receipt of an intermediate pulse, moves said first member means into said first position and said second member means into said fourth position.

6. The improvement of claim 5 wherein said variable rate divider means provides no more than one output pulse for each intermediate pulse it receives from said binary divider means.

7. The improvement of claim 2 wherein said moving means operates on a source of electric current and wherein said responding means includes savings means, coupled (1) to said moving means and (2) to said source of electric current, said binary divider means, and said variable rate divider means, for limiting the time that current flows to said moving means when said moving means changes the positions of said first member means and said second member means to a period of less than one half the duration of the shorter of said intermediate pulses and said output pulses.

8. The improvement of claim 7 wherein said moving means includes first and second switching means each having a conducting state and a nonconducting state, said first and second switching means being connectable to said source of electric current and being coupled to said saving means, said saving means placing said first switching means in its conducting state during the time said moving means moves said first member means from said first position to said second position and placing said first switching means in its nonconducting state at substantially all other times, said saving means placing said second switching means in its conducting state during the time said moving means moves said second member means from said third position to said fourth position and placing said second switching means in its nonconducting state at substantially all other times.

9. The improvement of claim 8 wherein said controller includes (1) a light coupled to said source of electric current for indicating that the voltage of said source of current is below a predetermined magnitude and (2) third switching means having conducting and nonconducting state and connected between said source of current and said light, with said third switching means also being coupled to said binary rate divider, said third switching means, during the receipt of a pulse from said binary rate divider, assuming one of its nonconducting or conducting states and, during the time when said switching means receives no pulse from said binary rate divider, assuming the other of its nonconducting and conducting states.

10. A fluid-flow limiting combination having:
(a) a casette with:
(1) metering means for holding a predetermined volume of fluid;
(2) closable inlet means, in fluid communications with said metering means, for permitting the flow of a fluid into said metering means; and
(3) closable outlet means, in fluid communication with said metering means, for permitting the flow of a fluid out of said metering means,
(b) a controller with:
(1) first member means, movable between a first position and a second position, for, when in said second position, closing said inlet means;
(2) second member means, movable between a third position and a fourth position, for, when in said fourth position, closing said outlet means;
(3) moving means, coupled to said first member means and said second member means, for moving said first member means between said first and second positions and said second member means between said third and fourth positions; and
(4) regulating means coupled to said moving means for controlling the operation of said moving means, the improvement wherein said regulating means comprises:
(A) crystal controlled oscillating means for producing digital pulses at a predetermined first frequency of less than 1 MHz;
(B) digital gate means, coupled to said oscillating means, for, upon the receipt of pulses of said first frequency from said oscillating means, providing output pulses at a second frequency which is less than half of said first frequency; and
(C) responding means, coupled to said gate means and to said moving means, for, upon the receipt of an output pulse from said gate means, causing said moving means to either move said first member means between said first and second positions or move said second member means between said third and fourth position; and wherein said digital gate means includes (1) binary divider means, coupled to to said oscillating means, for producing, at regular intervals, intermediate pulses equal in number of the number of electronic pulses divided by a positive integral power of two and (2) variable rate divider means, coupled to said binary divider means, for producing said second predetermined number of said outlet pulses with said second predetermined number being less than one third the number of said intermediate pulses, and wherein said responding means receives said intermediate pulses and said output pulses, and, upon the receipt of an output pulse, causes said moving means either (i) to move said first member means into said second position and said second member means into said third position or (ii) to move said first member means into said first position and said second member means into said fourth position, and upon the receipt of an intermediate pulse, causes said moving means to move said first and second member means in the opposite direction than upon the receipt of an output pulse.

11. The improvement of claim 10 wherein said first frequency is selected from the group consisting of 100,000 Hz., 76,800 Hz., 60,000 Hz., 40,960 Hz., 38,400 Hz., 32,768 Hz., 31,500 Hz., 30,720 Hz., 20,480 Hz., 19,200 Hz., 18,641 Hz., 16,384 Hz., 16,000 Hz., 15,360 Hz., 12,800 Hz., 10,000 Hz.

12. The improvement of claim 11 wherein said controller is used with a cassette in which said metering chamber has a deliverable volume of 0.2898 ml.

13. In a controller having:
(1) a first elongated rigid member movable between a first position and a second position;
(2) a second elongated rigid member movable between a third and a fourth position;
(3) moving means coupled to said first and second members for moving said first member between said first and said second position and for moving said second member between a said third and said fourth position; and
(4) regulating means, coupled to said moving means, for controlling the operation of said moving means, the improvement wherein said regulating means comprises:
(A) crystal controlled oscillating means for producing digital pulses at a predetermined first frequency of less than 1 MHz;
(B) digital gate means coupled to said oscillating means for, upon the receipt of pulses at said first frequency from said oscillating means, providing output pulses at a second frequency which is less than half of said first frequency; and
(C) responding means coupled to said gate means and moving means to either move said first member between said first and second positions or move said second member between said third and fourth positions; and wherein said digital gate means includes (1) binary divider means, coupled to said oscillating means, for producing, at regular intervals, intermediate pulses equal in number of the number of electronic pulses divide by a positive integral power of two and (2) variable rate divider means, coupled to said binary divider means, for producing said second predetermined number of said output pulses with said second predetermined number being less than one third the number of said intermediate pulses, and wherein said responding means receives said intermediate pulses and said output pulses, and, upon the receipt of an output pulse, causing said moving means either (i) to move said first member means into said second position and said second member means into said third position or (ii) to move said first member means into said first position and said second member means into said fourth position, and upon the receipt of an intermediate pulse, causes said moving means to move said first and second member means in the opposite direction than upon the receipt of an output pulse.

14. The improvement of claim 13 wherein said first frequency is selected from the group consisting of 100,000 Hz., 76,800 Hz., 60,000 Hz., 40,960 Hz., 38,400 Hz., 32,768 Hz., 31,500 Hz., 30,720 Hz., 20,480 Hz., 19,200 Hz., 18,641 Hz., 16,384 Hz., 16,000 Hz., 15,360 Hz., 12,800 Hz., 10,000 Hz.

15. In a controller for use with a casette having:
(a) metering means for holding a predetermined volume of a fluid;
(b) closable inlet means, in fluid communication with said metering means, for permitting the flow of a fluid into said metering means; and
(c) closable outlet means, in fluid communication with said metering means, for permitting the flow of a fluid out of said metering means, said controller having:
(a) first member means, movable between a first position and a second position, for, when in said second position, closing said inlet means;
(b) second member means, movable between a third position and a fourth position, for, when in said fourth position, closing said outlet means;
(c) moving means, coupled to said first member means and said second member means, for moving said first member means between said first and second positions and said second member means between said third and fourth positions; and
(d) regulating means, coupled to said moving means, for controlling the operation of said moving means, the improvement wherein said regulating means comprises:
(A) pulsing means for producing electronic pulses at a predetermined first frequency;
(B) pulse absorbing means, coupled to said pulsing means, for, upon the receipt of a first predetermined number of said electronic pulses, producing a second predetermined number of output pulses, said second predetermined number not being greater than half said first predetermined number, said pulse absorbing means, after producing a first output pulse, not producing a second output pulse until it has received two of said electronic pulses after the start of said first output pulse; and
(C) responding means, coupled to said pulsing means and to said pulse absorbing means, for, (1) upon the receipt of one of said output pulses, causing said moving means to place said first member means in said first position and said second member means in said fourth position and, (2) upon the receipt of one of said electronic pulses not any part of which occurs during an output pulse, causing said moving means to place said first member means in said second position and said second member means in said third position.

16. The improvement of claim 15 wherein said pulse absorbing means includes selection means for changing said second predetermined number.

17. The improvement of claim 16 wherein said pulsing means includes (i) oscillating means for producing initial pulses at a predetermined third frequency which is at least twice said predetermined first frequency and (ii) a rate divider coupled to said pulsing means and said pulse absorbing means for, upon the receipt of said initial pulses, producing said electronic pulses at said predetermined first frequency.

18. The improvement of claim 16 wherein said electronic pulses have a regular period and wherein said responding means includes gate means with input connections coupled to said pulse absorbing means and to said pulsing means and output connections coupled to said moving means for, upon the receipt of an output pulse, producing a first electronic state at said output connections and, upon the receipt of an electronic pulse, producing a second electronic state at said output connections, said first and second electronic states each having a duration of at least one and one half times said regular period of said electronic pulses.

19. The improvement of claim 18 wherein said gate means begins said first state at the conclusion of one of said electronic pulses and continues said first electronic state until the end of the electronic pulse immediately succeeding said one of said electronic pulses.

20. The improvement of claim 19 wherein (1) said moving means, when said gate means produces said first electronic state, either moves said first member means into said second position and said second member means into said third position or moves said first member means into said first position and said second member means into said fourth position, and (2) when said gate means produces said second electronic state, moves said first and second member mean in the opposite direction than upon the receipt of an output pulse.

21. The improvement of claim 20 wherein said pulsing means, said absorbing means, and said responding means each includes eleelectronic logic components, with all of said electronic logic components being CMOS components.

22. The improvement of claim 21 wherein (1) said moving means operates on a source of electronic current, (2) said responding means includes saving means coupled to said gate means and to said moving means for limiting the times that current flows to said moving means when said moving means changes the positions of said first and second member means to a period of less than one half the duration of the shorter of said electronic pulses and said output pulses, and (3) said moving means includes first and second switching means each having a conducting state and a nonconducting state, said first and second switching means being connectable to said source of electric current and being coupled to said saving means, said saving means placing said first switching means in its conducting state during the time said moving means moves said first member means from said first position to said second position and placing said first switching means in its nonconducting state at substantially all other times, said saving means placing said second switching means in its conducting state during the time said moving means moves said second member means from said third position to said fourth position and placing said second switching means in said nonconducting state at substantially all other times.

23. The improvement of claim 22 wherein said gate means includes a D-type flip-flop with the output of said absorbing means being coupled to the S input to said flip-flop, the C input of said flip-flop being coupled to said rate divider, and the D and R inputs of said flip-flop being coupled to ground.

24. The improvement of claim 19 wherein, when said pulse absorbing means produces, upon the receipt of said first predetermined number of said electronic pulses, a second predetermined number of putput pulses not greater than one third of said first predetermined number, and said pulse absorbing means, after producing a first output pulse, produces no second output pulse until it has received three of said electronic pulses after the start of said first output pulse.

25. The improvement of claim 19 wherein said regulating means has a ground voltage, said electronic pulses and said output pulses have the same duration and the same polarity relative to said ground voltage, and each of said output pulses begins at the end of one of said electronic pulses and ends at the beginning of the electronic pulse succeeding said one electronic pulse.

26. The improvement of claim 25 wherein, when said moving means moves said first member means from said second position to said first position, it does so only at the end of a produced electronic pulse, at which time same moving means also moves said second member means from said third position to said fourth position, and, at the beginning of the second succeeding electronic pulse after said produced electronic pulses, said moving means moves said first member means from said first position to said second position and said second member means from said fourth position to said third position.

27. The improvement of claim 19 wherein said oscilator means includes a crystal controlled oscillator having a frequency selected from the group consisting of 100,000 Hz., 76,800 Hz., 60,000 Hz., 40,960 Hz., 38,400 Hz., 32,768 Hz., 31,500 Hz., 30,720 Hz., 20,480 Hz., 19,200 Hz., 18,641 Hz., 16,384 Hz., 16,000 Hz., 15,360 Hz., 12,800 Hz., 10,000 Hz., and wherein said predetermined first frequency of said electronic pulses produced by said pulsing means is equal to said predetermined third frequency of said initial pulses produced by said oscillating means divided by a positive integral power of two.

28. In a fluid-flow limiting combination having:
(a) a casette with:
(1) metering means for holding a predetermined volume of a fluid;
(2) closable inlet means, in fluid communications with said metering means, for permitting the flow of a fluid into said metering means,
(3) closable outlet means in fluid communication with said metering means for permitting the flow of a fluid out of said metering means; and
(b) a controller with:
(a) first member means, movable between a first position and a second position, for, when in said second position, closing said inlet means;
(b) second member means, movable between a third position and a fourth position for, when in said fourth position, closing said outlet means;
(c) moving means, coupled to said first member means and said second member means, for moving said first member means between said first and second positions and said second member means between said third and fourth positions; and
(d) regulating means, coupled to said moving means, for controlling the operation of said moving means, the improvement wherein said regulating means comprises:
(A) pulsing means for producing electronic pulses at a predetermined first frequency;
(B) pulse absorbing means, coupled to said pulsing means, for, upon the receipt of a first predetermined number of said electronic pulses, producing a second predetermined number of output pulses, said second predetermined number not being greater than half said first predetermined number, said pulse absorbing means, after producing a first output pulse, not producing a second output pulse until it has received two of said electronic pulses after the start of said first output pulse; and
(C) responding means, coupled to said pulsing means and to said pulse absorbing means, for (1), upon the receipt of one of said output pulses, causing said moving means to place said first member means in said first position and said second member means in said fourth position and (2), upon the receipt of one of said electronic pulses not any part of which occurs during an output pulse, causing said moving means to place said first member means in said second position and said second member means in said third position.

29. The improvement of claim 28 wherein said pulse absorbing means includes selection means for changing said second predetermined number.

30. The improvement of claim 29 wherein (1) said electronic pulses have a regular period, (2) said pulsing means includes (i) oscillating means for producing initial pulses at a predetermined third frequency which is at least twice said predetermined first frequency and (ii) a rate divider coupled to said pulsing means and said pulse absorbing means for, upon the receipt of said initial pulses, producing said electronic pulse at said predetermined first frequency, (3) said responding means includes gate means, with input connections coupled to said pulse absorbing means and to said rate divider and output connections coupled to said moving means, for, upon the receipt of an output pulse, producing a first electronic state at said output connections and, upon the receipt of an electronic pulse, producing a second state at said output connections, said first and second electronic states each having a duration of at least one and one half times said regular period of said electronic pulses, (4) said gate means begins said first state at the conclusion of one of said electronic pulses and continues said first electronic state, begun at said one electronic pulses, until the end of the electronic pulse immediately succeeding said one electronic pulse.

31. The improvement of claim 30 wherein said oscillating means, said pulse absorbing means, and said responding means each includes electronic logic components, with all of said electronic logic components being CMOS components.

32. The improvement of claim 31 wherein said gate means includes a D-type flip-flop with the output of said rate divider being coupled to the S input to said flip-flop, the C input of said flip-flop being coupled to said rate divider, and the D and R inputs of said flip-flop being coupled to ground.

33. The improvement of claim 32 wherein said pulse absorbing means produces, upon the receipt of said first predetermined number of said electronic pulses, a second predetermined number of said output pulses not greater than one third of said first predetermined number, and said pulse absorbing means, after producing a first output pulse, produces no second output pulse until it has received three of said electronic pulses after the start of said first output pulse.

34. The improvement of claim 33 wherein (1) said regulating means has a ground voltage, (2) said electronic pulses and said output pulses have the same duration and the same polarity relative to said ground voltage, (3) each of said output pulses begins at the end of one of said electronic pulses and ends at the beginning of the electronic pulse succeeding said one electronic pulse, and (4) when said moving means moves said first member means from said second position to said first position, it does so only at the end of a produced electronic pulse, at which time said moving means also moves said second member means from said third position to said fourth position, and, at the beginning of the second succeeding electronic pulse after said produced electronic pulse, said moving means moves said first member means from said first position to said second position and said second member means from said fourth position to said third position.

35. The improvement of claim 34 wherein said controller is used with a casette in which said metering chamber has a volume of 0.2898 ml.

36. In a controller having:
(1) a first elongated rigid member, movable between a first position and a second position;
(2) a second elongated rigid member, movable between a third position and a fourth position; and
(3) moving means, coupled to said first and second members for moving said first member between a first position and a second position and for moving said second member between a third position and a fourth position; and
(4) regulating means, coupled to said moving means, for controlling the operation of said moving means, the improvement wherein said regulating means comprises:
(A) pulsing means for producing electronic pulses at a predetermined first frequency;
(B) pulse absorbing means, coupled to said pulsing means, for, upon the receipt of a first predetermined number of said electronic pulses, producing a second predetermined member of output pulses, said second predetermined number not being greater than half said first predetermined number, said pulse abosrbing means, after producing a first output pulse, not producing a second output pulse until it has received two of said electronic pulses after the start of said first output pulse; and
(C) responding means, coupled to said pulsing means and to said pulse absorbing means, for (1), upon the receipt of one of said output pulses, causing said moving means to place said first member means in said first position and said second member means in said fourth position and (2), upon the receipt of one of said electronic pulses not any part of which occurs during an output pulse, causing said moving means to place said first member means in said second position and said second member means in said third position.

37. The improvement of claim 36 wherein said pulse absorbing means includes selection means for changing said second predetermined number.

38. The improvement of claim 37 wherein (1) said electronic pulses have a regular period, (2) said pulsing means includes (i) oscillating means for producing initial pulses at a predetermined third frequency which is at least twice said predetermined first frequency and (ii) a rate divider coupled to said pulsing means and said pulse absorbing means for, upon the receipt of said initial pulses, producing said electronic pulse at said predetermined first frequency, (3) said responding means includes gate means, with input connections coupled to said pulse absorbing means and to said rate divider and output connections coupled to said moving means, for, upon the receipt of an output pulse, producing a first electronic state at said output connections and, upon the receipt of an electronic pulse, producing a second state at said output connections, said first and second electronic states each having a duration of at least one and one half times said regular period of said electronic pulses, (4) said gate means begins said first state at the conclusion of one of said electronic pulses and continue said first electronic state, begun at said one electronic pulses, until the end of the electronic pulse immediately succeeding said one electronic pulse.

39. The improvement of claim 38 wherein said pulse absorbing means produces, upon the receipt of said first predetermined number of said electronic pulses, a second predetermined number of output pulses not greater than one third of said first predetermined number, and said pulse absorbing means, after producing a first output pulse, produces no second output pulse until it has received three of said electronic pulses after the start of said first output pulse.

40. The improvement of claim 39 wherein said predetermined first frequency at which said pulsing means produces said electronic pulses does not exceed one per second and said pulse absorbing means, when receiving said electronic pulses, produces at least one of said output pulses after a period not exceeding about one minute after the production of the immediately prior output pulse.

* * * * *